United States Patent
Kim et al.

(12) 
(10) Patent No.: US 6,187,590 B1
(45) Date of Patent: Feb. 13, 2001

(54) HEMATOLOGY REFERENCE CONTROL AND METHOD OF PREPARATION

(75) Inventors: Young Ran Kim, Sunnyvale; Jean Emiko Kihara, San Jose, both of CA (US)

(73) Assignee: Abbott Laboratories, Abbott Park, IL (US)

(*) Notice: Under 35 U.S.C. 154(b), the term of this patent shall be extended for 0 days.

(21) Appl. No.: 09/173,823

(22) Filed: Oct. 16, 1998

Related U.S. Application Data

(62) Division of application No. 08/673,672, filed on Jun. 26, 1996, now Pat. No. 5,858,790.

(51) Int. Cl.⁷ .................................................. G01N 31/00
(52) U.S. Cl. ................................. 436/10; 436/8; 436/16; 436/17; 436/18; 436/63; 436/164; 436/166; 436/175
(58) Field of Search .................................. 436/63, 16, 17, 436/18, 8, 10, 166, 174, 175; 435/2

(56) References Cited

U.S. PATENT DOCUMENTS

| | | |
|---|---|---|
| 3,632,735 | 1/1972 | Kita et al. . |
| 4,219,440 * | 8/1980 | Runck ................................... 252/408 |
| 4,698,312 * | 10/1987 | Wong ..................................... 436/10 |
| 4,704,364 | 11/1987 | Carver et al. . |
| 4,777,139 * | 10/1988 | Wong ..................................... 436/18 |
| 4,847,204 | 7/1989 | Mitzner et al. . |
| 5,262,327 | 11/1993 | Ryan . |
| 5,320,964 | 6/1994 | Young et al. . |
| 5,380,664 * | 1/1995 | Carver ................................... 436/10 |
| 5,516,695 | 5/1996 | Kim et al. . |
| 5,529,933 * | 6/1996 | Young ..................................... 436/10 |
| 5,559,037 | 9/1996 | Kim et al. . |
| 5,677,145 | 10/1997 | Ryan . |

FOREIGN PATENT DOCUMENTS 9618878 6/1996 (WO) .

OTHER PUBLICATIONS

Cornbleet, P. J., et al., "Evaluation of the Cell–Dyn 3000 Differential", *Amer. Journ. Of Clin. Pathology*, 98(6)::604–614, 1992.

Van Hove, et al., "Cell–Dyn 4000®, A New Generation Hematology Analyzer", *Anemias, Disorders of Nutrients, Disordered Red Cell Production*, 14b:2784, 1996.

* cited by examiner

*Primary Examiner*—Maureen M. Wallenhorst
(74) *Attorney, Agent, or Firm*—Mimi C. Goller

(57) ABSTRACT

Hematology reference control cells and method of manufacture. The invention relates to the methods of preparing stable white blood cell ("WBC") and nucleated red blood cell ("NRBC") fractions and the hematology control reagents containing such stablized cells for primary use on a multi-angle light scatter based hematology instrument.

3 Claims, 19 Drawing Sheets

HEMATOLOGY REFERENCE CONTROL AND METHOD OF PREPARATION

This is a division of U.S. patent application Ser. No. 08/673,672, filed Jun. 26, 1996, now U.S. Pat. No. 5,858,790, issued on Jan. 12, 1999.

BACKGROUND

This invention relates to hematology control compositions and their methods of preparation and use in a reference standard. More particularly, this invention relates to a hematology reference control suspension containing stabilized white blood cells ("WBC") and the nuclei of mammalian WBC or avian or fish erythrocytes. Even more particularly this invention relates to a hematology reference control suspension containing stabilized WBC that have been subjected to a whole blood lysing process during their preparation such that in their stabilized state they retain multi-angle light scattering properties. This enables the stablized cells, when utilized in a hematology analyzer that differentiates WBC based solely on multi-angle light scatter signals to produce multi-angle light scatter signal that mimic whole blood WBC signals. Currently there are several different brands of automated hematology instruments in the marketplace. These different analyzers utilize varying detection techniques to quantify neutrophils, lymphocytes, monocytes, eosinophils and basophils. Among the detection techniques utilized are: electronic impedance, forward light scatter, polarized 90° angle light scatter, depolarized 90° angle light scatter, light absorption, radio-frequency and combinations thereof. The different optical bench designs significantly affect the characteristics of the optical signals obtained from stabilized control cells. Since these instruments utilize different detection methods for white blood cell differential analysis ("WBC/Diff"), it has become necessary to utilize different types of WBC/Diff control solutions in order to obtain control cell signatures that are similar to those of whole blood cells when run on that particular type of instrument.

The current class of instruments must utilize either impedance, impedance and light scatter (but not necessarily multi-angle light scatter), or light scatter, impedance and radio frequency signals to differentiate and determine cells from one another. Further, these currently available hematology instruments are not able to quantify nucleated red blood cells ("NRBC"). NRBC interfere with an accurate WBC/Diff analysis. The currently available hematology instruments only "flag" for the existence of NRBC in a sample. However, the soon to be released Abbott Cell-Dyn® 4000 hematology analyzer system will be capable of performing a simultaneous whole blood analysis of WBC/Diff and NRBC. The Cell-Dyn® 4000 instrument will perform a simultaneous, whole blood analysis by utilizing only multi-angle light scatter signals, including on occasion fluorescence to differentiate among WBC and NRBC. Consequently, it has become necessary to develop a new hematology control for WBC/Diff and NRBC analysis. The control cells of this new reference control must possess all of the multi-angle light scattering capabilities of the cells of the whole blood sample that they are suppose to mimic.

There are in the current realm of art, several patents which describe methods and reagent systems for preparing hematology reference control materials for the current class of analyzers, i.e. those that do not perform an exclusive multi-angle light scatter WBC/Diff analysis. The applicants are not aware of any art describing a method or reagent system for the preparation or utilization of a hematology reference control for the multi-angle light scatter analysis of WBC or NRBC.

U.S. Pat. No. 4,704,364 to Carver et al. and assigned to Coulter Instrument Corp., discloses a method for preparing a three component system which simulates the three major components of human leukocytes. However these simulated cells are detected by an impedance based detection system, not a multi-angle light scatter detection system. Carver et al. use fixed, red blood cells ("RBC") from the nurse shark to simulate human granulocytes; fixed RBC from turkeys to simulate human mononuclear cells; and fixed human RBC to simulate human lymphocytes. The hematology control produce by the teachings of Carver et al. is useful only for electronic impedance measurement of a 3 part WBC/Diff since the three components are only distinguishable by size (impedance), not by optical properties.

The three components produced by Carver et al.'s method do not have similar cell surface structure or cytoplasmic granularity substantially the same as that of human WBC. Therefore, they are not usable as a reference control on a multi-angle light scatter based system. The applicants tested these simulated cells on the soon to be commercially available Cell-Dyn® 4000 analyzer, and found that the light scattering characteristics of the simulated WBC in the Carver et al. control produced very different multi-angle light scatter signals than that of a normal blood sample. FIGS. 1a–1c are reproductions of the dot plots obtained on a Cell-Dyn® 4000 hematology analyzer for normal blood.

[Abbreviations used to label the axis in the following figures:

| | |
|---|---|
| ALL or WBC ALL: | Axial Light Loss (0°) |
| IAS or WBC IAS: | Intermediate Angle Scatter (3°–10°) |
| PSS or WBC PSS: | Polarized Light Scatter (90°) |
| DSS or WBC DSS: | Depolarized Light Scatter (90°) |
| FL3 or WBC FL3: | Red Fluorescence (515–545 nm) |
| G: | Granulocyte Cluster |
| M: | Monocyte Cluster |
| B: | Basophil Cluster |
| L: | Lymphocyte Cluster |
| E or Eos: | Eosinophil Cluster |
| N: | Neutrophils |
| S: | Noise signals from RBC Stroma & PLT |
| NRBC: | Nucleated Red Blood Cells |

FIGS. 4a–4c show the results obtained on a Cell Dyn® 4000 analyzer for the simulated WBC control of Carver et al. and embodied in the Coulter Corp. Product 4C® Plus Cell control. As can be seen in FIGS. 4a–4c the clusters are not identifiable.

U.S. Pat. No. 5,270,208 to Ryan, discloses a different method of preparing a hematology reference control for WBC/Diff analysis. In the Ryan method, aldehyde-fixed human WBC's are suspended in an isotonic aqueous medium comprising lipoprotein in an amount sufficient to provide a mixture that gives a WBC signature profile that is substantially similar to that obtained from whole blood. To support his claim, Ryan exhibited a WBC distribution of a Coulter Corp. STK-S® analyzer dot plot, DF1 (abscissa) vs. Volume (ordinate). It is believed that Ryan's WBC preparation is commercially available under the name of PARA 12® (Low, Normal & High) Tri-level hematology control from Streck Laboratories. The applicants tested this commercial material on a Cell-Dyn® 4000 analyzer which performs a simultaneous analysis of WBC/Diff and NRBC by multi-angle light scatter (axial light loss, multi-dimensional light scatter and fluorescence.) The results (see FIGS. 5a–5c) reveal that the WBC component of the Ryan preparation generates a significantly different light scatter signature than that obtained from whole blood. As can be seen in FIGS. 5a–5c the neutrophil components of the product generated much smaller axial light loss and polarized side scatter signals than that of whole blood; the depolarized side scatter signals from neutrophils are much too large to be separated from that of eosinophils; monocyte cluster does not separate from neutrophil cluster at all; the lymphocyte component generate much higher intermediate angle scatter (7°) signals than that of whole blood and thus wiping out the region reserved for basophils by overlapping.

U.S. Pat. No. 5,320,964 to Young et al. discloses methods and reagent compositions for preparing leukocyte analogs. The Young et al. lymphocyte analogs are prepared from fixed goose RBC in a hypotonic phosphate buffered solution (15–25 mOsm/kg); the Monocyte analogs are prepared from fixed alligator RBC in a hypotonic buffered solution (5–15 mOsm/kg); the Eosinophil analogs are also prepared from fixed alligator RBC in a hypotonic solution (75–85 mOsm/kg); and the Neutrophil analogs are prepared from alligator RBC in hypotonic buffered solution (45–65 mOsm/kg). Both goose RBC and alligator RBC are elliptical, nucleated and have a smooth cell surface. Young et al. claim that the fixed cells prepared according to their procedures simulate at least two different human leukocytes, each having at least two physical properties of a human leukocyte. These properties are selected from: a) volume measured by D.C. current; b) high frequency (RF) size; c) opacity; and d) light scatter. Although they did not specify the type of light scatter, the Young et al. simulated WBC components prepared from goose and alligator RBC do not have the same characteristics with regard to cell surface structure and cytoplasmic granularity as those of mammalian WBC. Consequently, these cells do not generate the multi-angle light scatter signals for polarized and depolarized 90° light scatter and axial light loss signals that are substantially equivalent, or similar to that of human whole blood WBC. Thus, the Young et al. product cannot be used as a hematology reference control on a sophisticated hematology instruments that utilizes multi-dimensional light scatter, axial light loss and fluorescence signals, such as the Cell-Dyn® 4000 analyzer, for WBC/Diff and NRBC quantification. In fact, if the cells of Young et al. are fixed in a hypotonic buffered solution one of two results will occur. First, if the osmolarity of the solution is very low (5–25 mOsm/kg) the cytoplasm of the cells will lyse. If, on the other hand, the osmolarity is about (85 mOsm/kg) the cell volume will expand.

FIGS. 18a–18d show the results of a multi-parameter, light scatter based analysis of a control cell solution containing fixed alligator RBC as the control cells. As can be seen the fixed alligator cells generate no detectable PSS signals; the IAS signals fall between the regions of lymphocytes and basophils; and the ALL signals are too low to be counted as either neutrophils or eosinophils.

FIGS. 6a–6c show the results of another commercially available control, R&D Systems, Inc. CBC-3k™ Hematology Controls. It is not known if the CBC-3k™ product has been patented. As shown, the clusters cannot be identified.

SUMMARY OF THE INVENTION

These and further features and advantages of the invention will be apparent from the following description of the preferred embodiments thereof.

One object of the present invention is to provide a hematology reference control on an automated hematology instruments such as the Abbott Laboratories Cell-Dyn® 3000 instrument which uses multi-dimensional light scatter WBC/Diff analysis.

Another objective of the present invention is to provide a hematology reference control on an automated hematology system such as the Abbott Laboratories Cell-Dyn® 4000 instrument which utilizes multi-dimensional light scatter, axial light loss and fluorescence for simultaneous analysis of WBC/Diff and NRBC.

Yet another objective is to provide a stable hematology reference control which contains stabilized RBC, Platelets, Neutrophils, Lymphocytes, Eosinophils, Basophils and NRBC components which can be used on an automated hematology instruments such as the Cell-Dyn® 4000 instrument which uses multi-dimensional light scatter, axial light loss and fluorescence for the simultaneous analysis of WBC/Diff and NRBC.

Broadly, the present invention relates to the method for the preparation of a stable WBC and NRBC component and the hematology reference control solution containing one or more of these components. The method produces hard-fixed and stabilized WBCs and simulated NRBCs which generate similar electro-optical signals to that of human whole blood cells, enabling a complete WBC/Diff/NRBC analysis using the same algorithms utilized on an analyzer for fresh human blood samples. The fixed WBC's and simulated NRBCs produced by the method of the present invention are clump-free and stable in an appropriate plasma-like medium for a long period of time under refrigeration and can be used as Hematology Controls for WBC/Diff/NRBC on a routine clinical hematology instrument, including those utilizing multi-parameter light scatter. These advantages represent a substantial improvement over the prior art.

BRIEF DESCRIPTION OF THE DRAWING

For a more complete understanding of the present invention, and the advantages thereof, reference is now made to the following descriptions taken in conjunction with the accompanying figures, in which.

DETAILED DESCRIPTION OF THE INVENTION

Figure 1A:
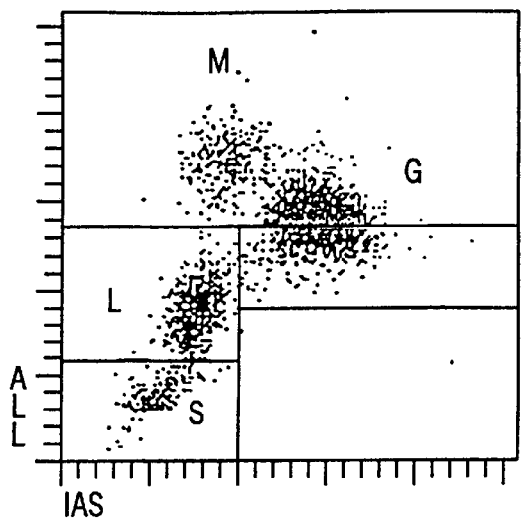
FIGS. 1a–1c are WBC cytograms of normal blood run on a multi-angle, light scatter based analyzer.
Figure 1B:
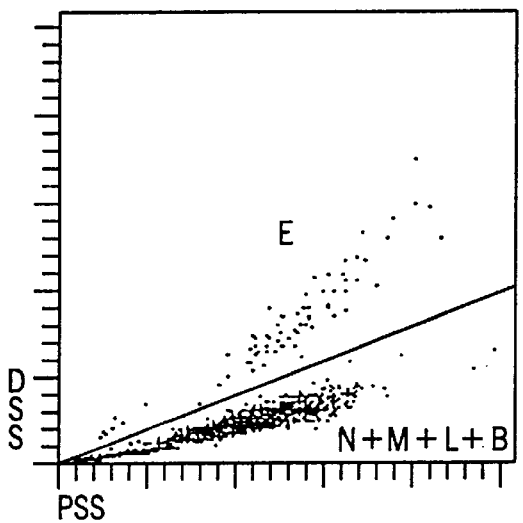
Figure 1C:
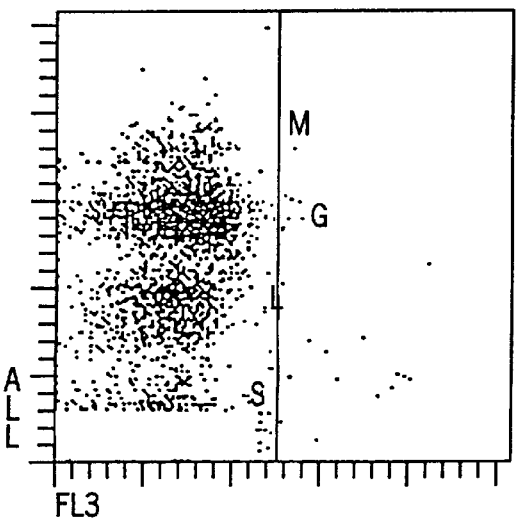
Figure 2A:
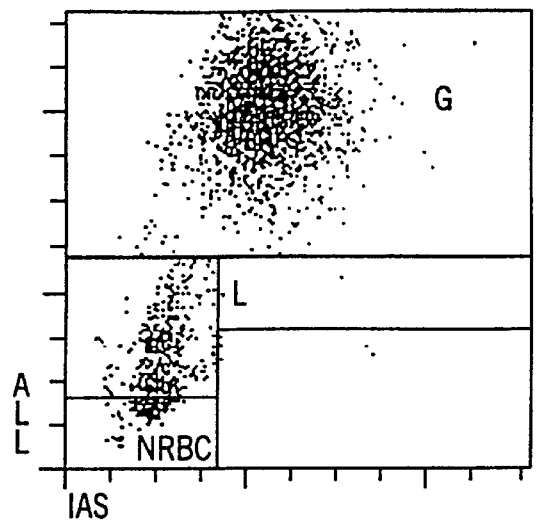
FIGS. 2a–2c are multi-angle light scatter based analyzer WBC/NRBC cytograms of a clinical sample containing 1.78 k/µL NRBC.
Figure 2B:
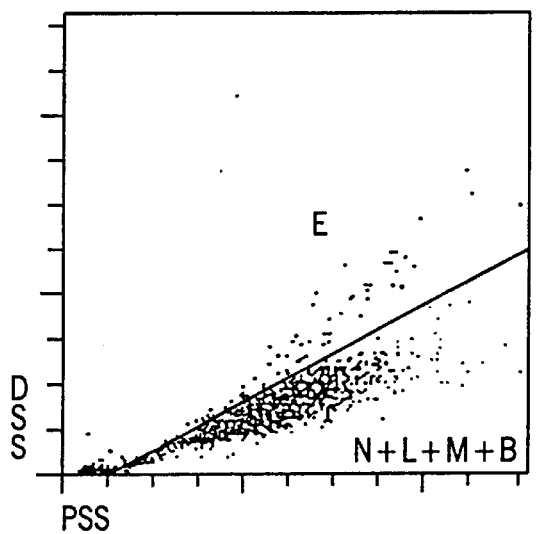
Figure 2C:
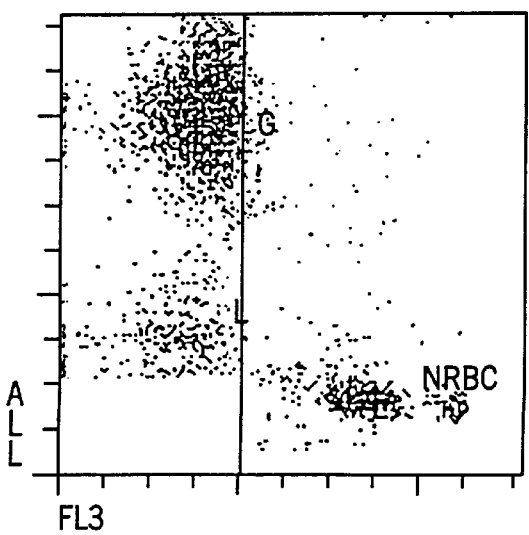
Figure 3A:
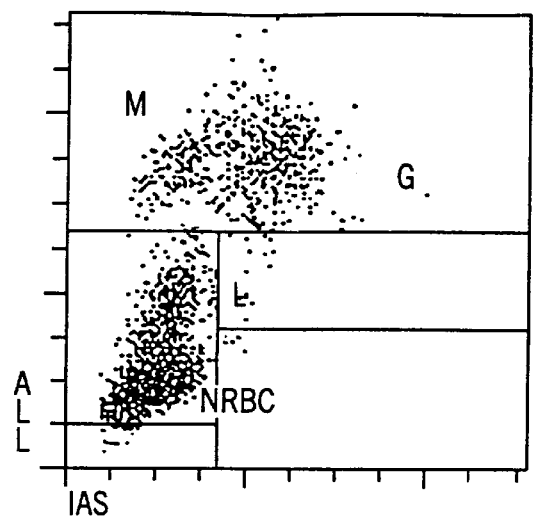
FIGS. 3a–3c are multi-angle, light scatter based analyzer WBC/NRBC cytograms of a clinical sample containing 40.4 k/µL NRBC.
Figure 3B:
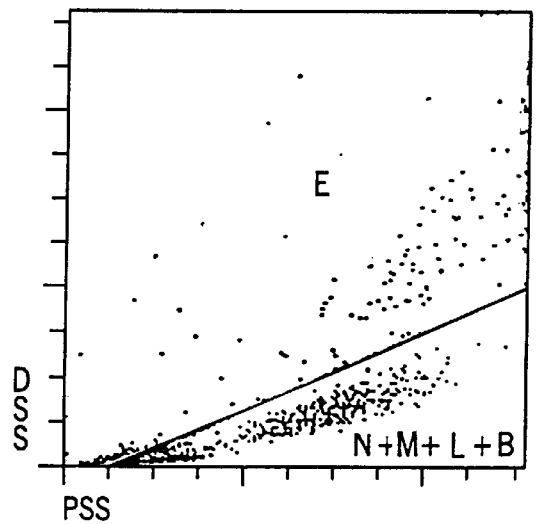
Figure 3C:
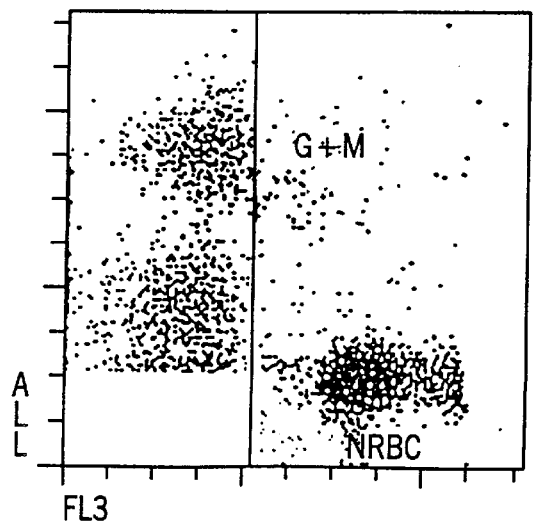
Figure 4A:
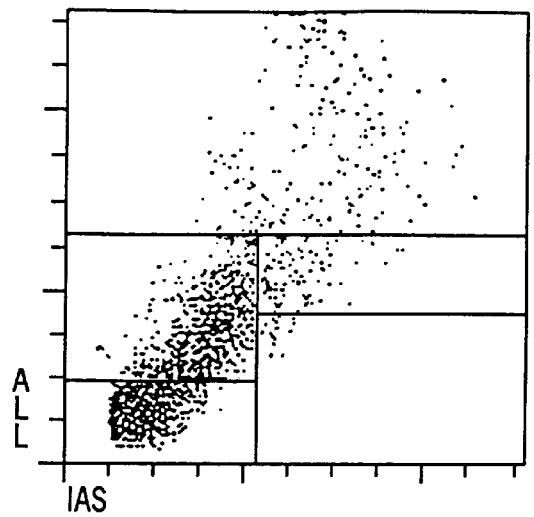
FIGS. 4a–4c are multi-angle, light scatter based analyzer WBC cytograms of Coulter® 4C® Plus Cell Controls.
Figure 4B:
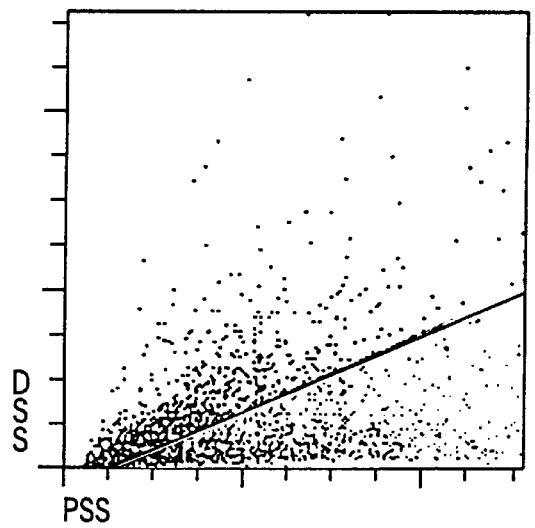
Figure 4C:
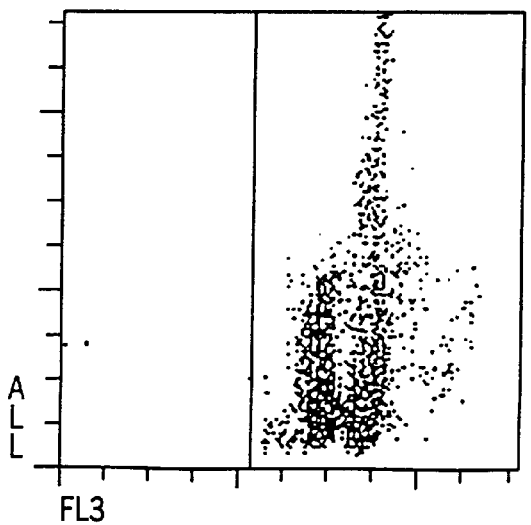
Figure 5A:
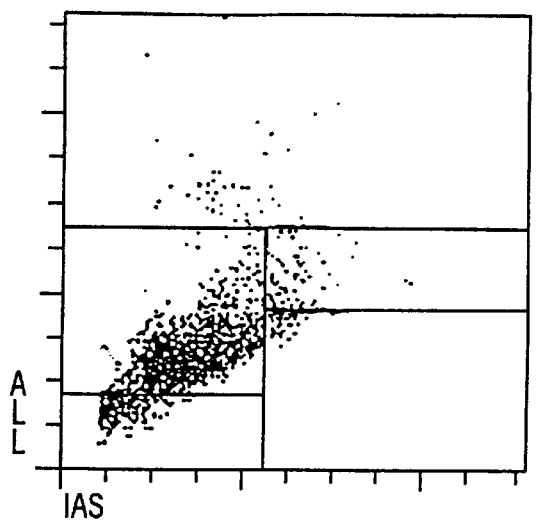
FIGS. 5a–5c are multi-angle, light scatter based analyzer WBC cytograms of Streck Laboratories' PARA 12® Multi-Parameter Hematology Controls, Normal Level.
Figure 5B:
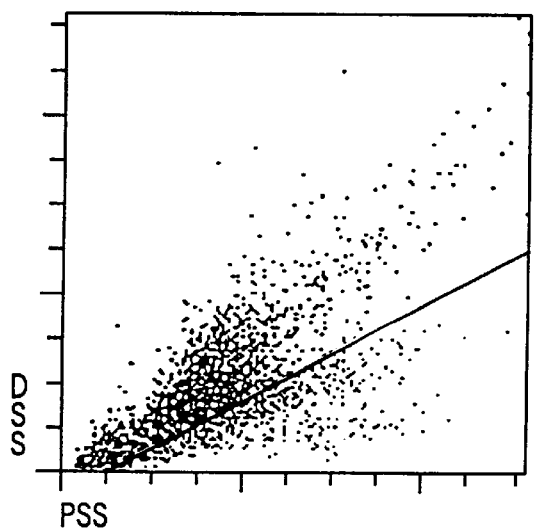
Figure 5C:
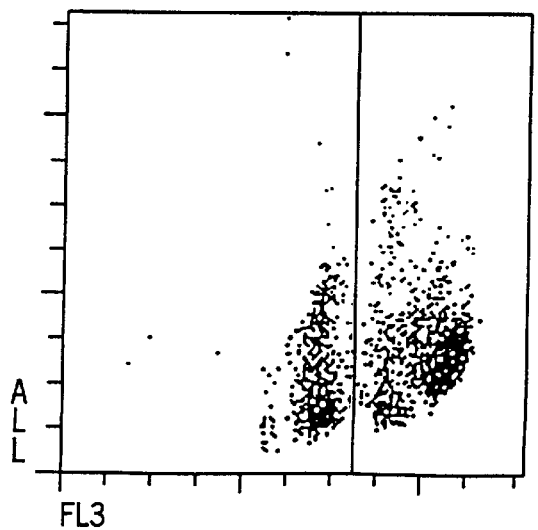
Figure 6A:
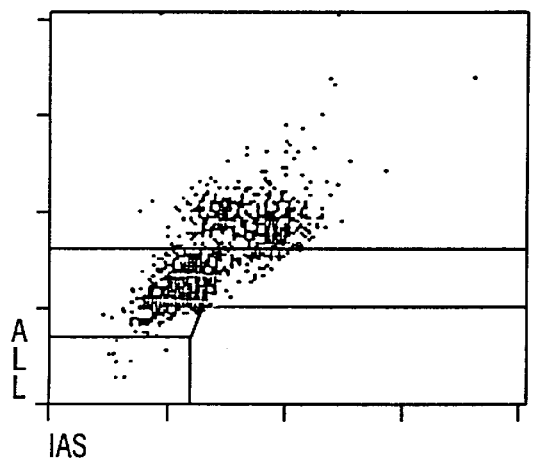
FIGS. 6a–6d are multi-angle, light scatter based analyzer WBC cytograms of R&D Systems' CBC-3K™ Hematology Controls.
Figure 6B:
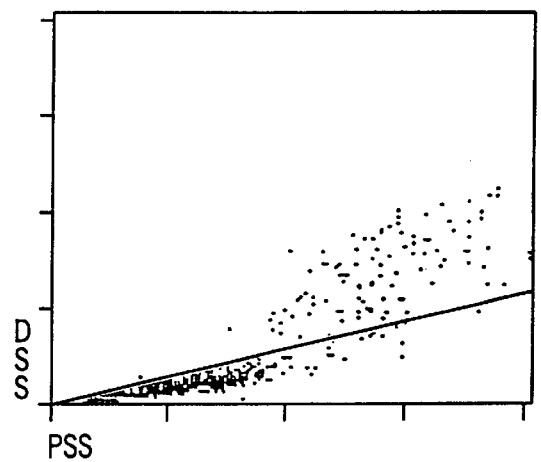
Figure 6C:
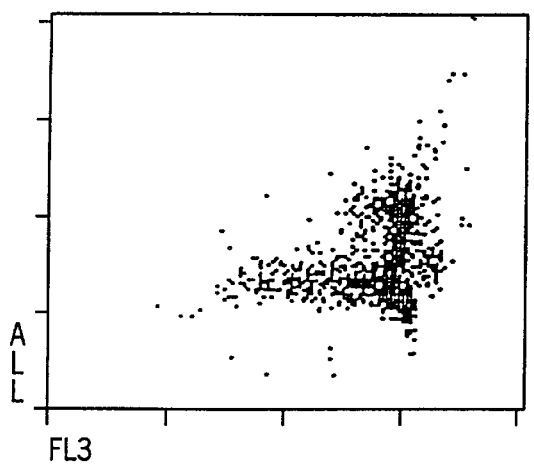
Figure 6D:
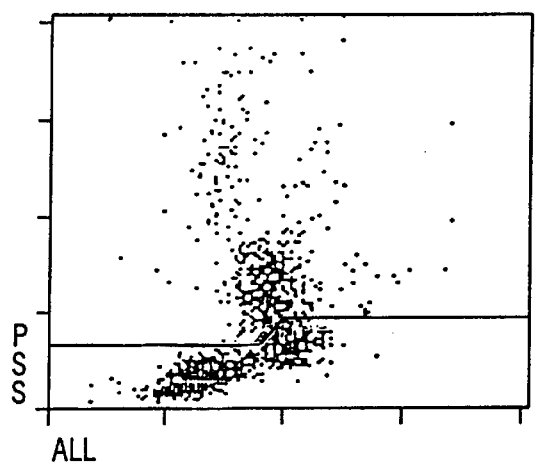

Any automated system for the detection and differentiation of cells requires the utilization of reference controls to assure that the system is operating properly. This is true no matter what detection system is employed.

With the advent of a new detection scheme, mainly that of utilizing only multi-angle/parameter light scatter signals to differentiate and distinguish WBC subpopulations and NRBC in a sample (to the exclusion of all other non-light signals), new controls have become necessary. Current, state of the art reference controls will not perform properly on such multi-parameter systems.

The present inventors have discovered why the current controls do not work on multi-angle light scatter based hematology analyzers and devised methods for producing controls that will work. Not only will the present invention controls perform on multi-parameter light scatter based systems, but they should also perform on other detection based systems as well. This is because the cells of the new controls are the same cells as is found in a blood sample, only processed. Therefore they retain the cell's light scattering characteristics.

The cellular components of the reference control suspensions of this invention substantially mimic the multi-parameter light scattering characteristics of the WBC or NRBC in a whole blood sample when run on a multi-parameter light scatter based detection system.

For the purposes of this invention multi-parameter, multi-angle, or multi-dimensional light scatter encompasses the exclusive use of (i.e., excludes non-) polarized and depo-larized 90° light scatter and axial light loss signals, and combinations thereof to determine or differentiate the cells of interest. No other non-light based signals are utilized for this determination. Other types of light signals may also be utilized, such as fluorescence, but impedance and other non-light based signals are not used. However, instruments which do use non-light based signals, or combinations of light scatter and impedance for example, can also benefit from the controls of this invention, but it is the multi-angle light scatter based instruments which will benefit the most as there are currently no such controls available.

The WBC components of the control suspension of this invention are WBC from blood that have been subjected to a very gentle lysing environment (similar to the environment they would have been subjected to in the analyzer had that blood sample been analyzed), and then fixed. The same is true for the NRBC components as well, the nuclei are exposed to a lysing environment and fixed to preserve their cellular characteristics. With the NRBC component however, mammalian nucleated blood cells are not the only cells that can be used as the source of the freed nuclei. Avian or fish erythrocytes can also utilized for this fraction.

The ability of the control cells to mimic the light scattering characteristics of the cells of interest is due to the fact that the cells are first chosen because of their cellular composition (i.e., their light scattering characteristics). During the manufacturing process these cellular components of the control cells are preserved by first subjecting them to a gentile lysing environment to lyse RBC; then the remaining WBC and NRBC nuclei are fixed before the lysing environment has destroyed the desired cellular characteristics. This manufacturing process mimics the environment "real" blood cells are subjected to in the interior passages of the analyzer. The control cells, because they are "fixed", are not significantly affected by the lysing environment when they pass through the analyzer, so they retain their desired characteristics. In addition, the fixed cells are stable in the control solution, where whole blood cells are not. However, it is believed that the control cells need to be subjected to the same or similar lysing environment that the blood cells in a sample while see in an analyzer in order to produce substantially the same refractive index, which primarily determines the light scattering characteristics of a cell. In this way the control cells will appear to the instrument to be the "instrument lysed" cells of interest and be recorded as such.

It has also been determined that the same cellular components of the present invention, if "fixed" prior to subjecting them to a lysing environment, do not perform satisfactorily in a multi-angle light scattering based system. The cells need to be subjected to a lysing environment before they are "fixed". Later, when they are processed as control cells in the analyzer these processed cells will "appear", to the analyzer, to be the blood cells of interest. This is because the multi-parameter light, scatter based analyzers are only programmed to recognize whole blood cells in the analyzer's internal processing environment. So, unless the reference control cells, or cellular components, retain the appropriate cellular characteristic and therefore, react or behave (scatter light and/or fluoresce) in a manner that is substantially similar to whole blood, they will "appear" to be different cells to the analyzer or be completely unrecognizable.

Therefore, the primary methods of this invention subject cells or cellular components to a lysing environment during the reference control manufacturing process and prior to their "fixation" that they will encounter in the analyzer when they are run as reference controls.

In the examples that follow the following reagent formulations were used:
Lysing Reagent:
    from about 0.75M to about 1.10M ammonium chloride (NH4Cl)

from about 0.1M to about 0.4M formaldehyde (HCHO)

from about 10 mM to about 25 mM sodium acetate (CH3COONa)

from about 10 mM to about 25 mM potassium bicarbonate (KHCO3)

from about 50 mg/L to about 250 mg/L Saponin from about 0.2 g/L to about 0.4 g/L Proclin 300

WBC-Cyto-Lyse:

from about 2.5 g/L to about 5.0 g/L maleic acid, succinic acid or phthalic acid from about 10.0 g/L to about 30.0 g/L Brij 35, Tween 20 or Triton X-100

Fixative:

from about 3.0 g/L to about 5.0 g/L monosodium phosphate from about 6.0 g/L to about 7.0 g/l disodium phosphate from about 100 ml/L to about 200 ml/L formalin (37–40% formaldehyde solution)

FIGS. 2a–2c and FIGS. 3a–3c are Abbott Laboratories Cell-Dyn® 4000 multi-parameter, light scatter based system cytograms of the WBC/NRBC distributions of clinical blood samples which contain 1.78 k/mL NRBC and 40.4 k/mL NRBC respectively. These Figures are presented for comparison purposes with the controls or cells produced by the various processes described and depicted in the Figures herein.

Since the fixed WBC and nuclei of avian, fish and mammalian cells of this invention are insert, they can be resuspended in any buffered saline, which may contain some protein to prevent clumping. However, these fixed cells need to be combined with unfixed, but stabilized RBC to produce a full range hematology control, the cell resuspending medium should be able to protect the stabilized RBC from lysis. The formulation below is an example of a resuspension medium that has been found to work well with the control cells of this invention. This formulation is a plasma-like cell resuspension medium that prevents clumping of fixed WBC and nuclei while protecting the RBC components in the control solution from lysis Plasma-like Cell Resuspension Medium (CRSM):

| Chemical | Conc. Range/L | Preferred Conc./L |
|---|---|---|
| Na$_2$HPO$_4$ | 2.20–2.70 g | 2.45 g |
| KH$_2$PO$_4$ | 0.36–0.44 g | 0.40 g |
| Na$_3$Citrate | 3.30–4.05 g | 3.68 g |
| Citric Acid | 0.41–0.51 | 0.46 g |
| Dextrose | 4.05–4.95 | 4.50 g |
| Mannose | 1.35–1.65 | 1.50 g |
| Adenine | 0.30–0.55 | 0.50 g |
| BSA* | 15.0–50.0 | 30.0 g |
| NaCl | adj. to 290 ± 15 mOsm/L | 0.50 g |
| Proclin 300 (Preservative) | 0.15–0.45 | 0.30 g |
| pH | adj. pH to 7.2 ± 0.2 with 1 N NaOH | adj. pH to 7.2 ± 0.2 with 1 N NaOH |
| Osmolarity | 290 ± 15 mOs/L | 290 ± 15 mOs/L |

*Fatty acid free bovine serum albumin

The use of hematology control produced by the method of present invention on Cell Dyn® 4000 hematology instrument, which analyzes WBC/Diff/NRBC by multi-dimensional light scatter, axial light loss and fluorescence, permits monitoring of day to day performance of the system as well as reagents. The parameters that the quality of the results can be monitored with the product on the Cell-Dyn® 4000 system are as follows:

| Parameter | Absolute Cell Counts | % of Total WBC |
|---|---|---|
| Total WBC | # of cells/mL | % of Total WBC |
| Neutrophils | # of cells/mL | % of Total WBC |
| Lymphocytes | # of cells/mL | % of Total WBC |
| Eosinophils | # of cells/mL | % of Total WBC |
| Monocytes | # of cells/mL | % of Total WBC |
| Basophils | # of cells/mL | % of Total WBC |
| NRBC | # of cells/mL | # of NRBC/100 WBC |

EXAMPLE 1

Figure 7A:
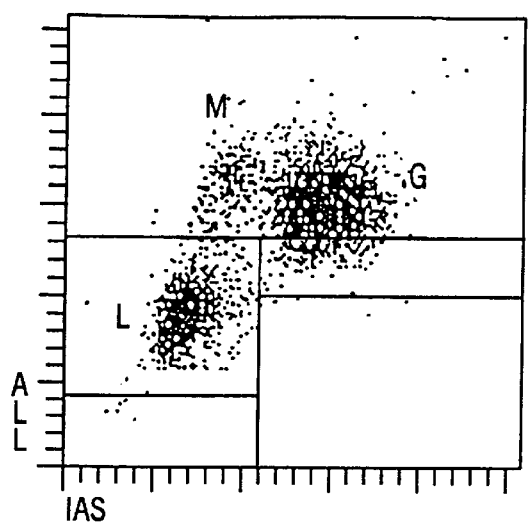
FIGS. 7a–7c are multi-angle, light scatter based analyzer WBC cytograms of the hematology reference control of the present invention.
Figure 7B:
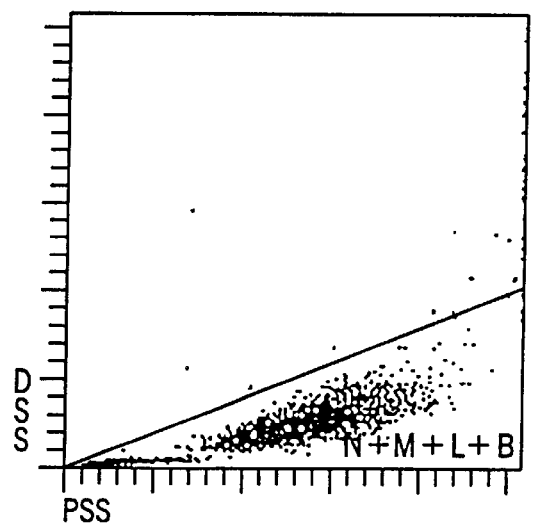
Figure 7C:
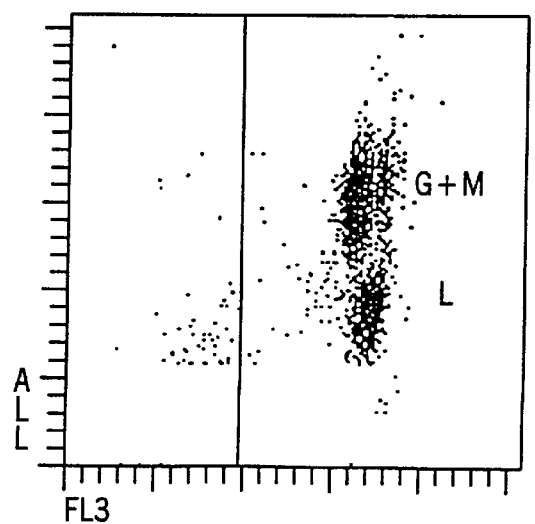
Figure 8A:
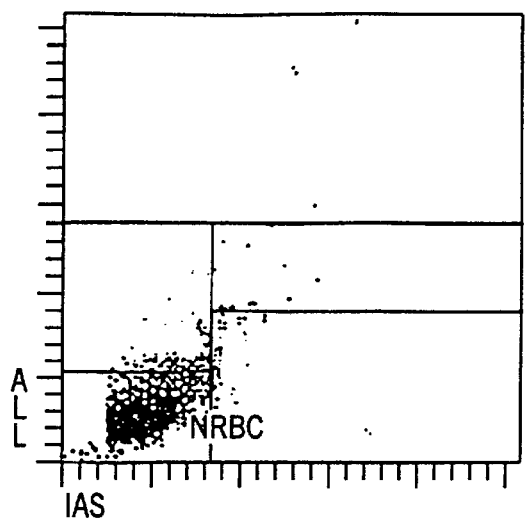
FIGS. 8a–8c are multi-angle, light scatter based analyzer WBC cytograms of fixed trout erythrocyte nuclei produced by the methods of the present invention.
Figure 8B:
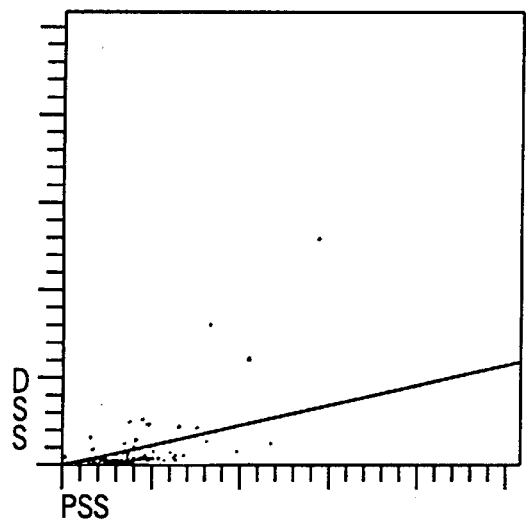
Figure 8C:
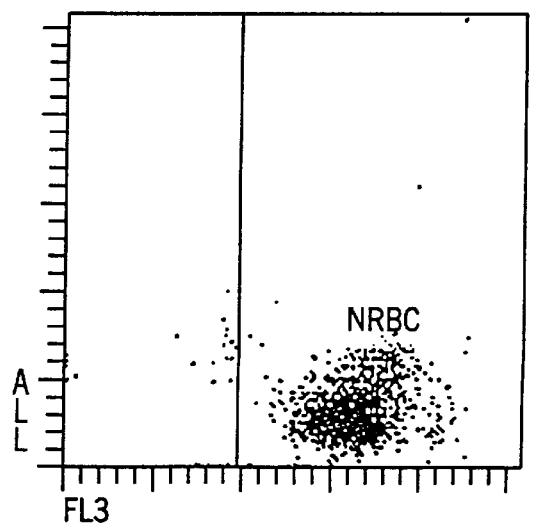
Figure 9A:
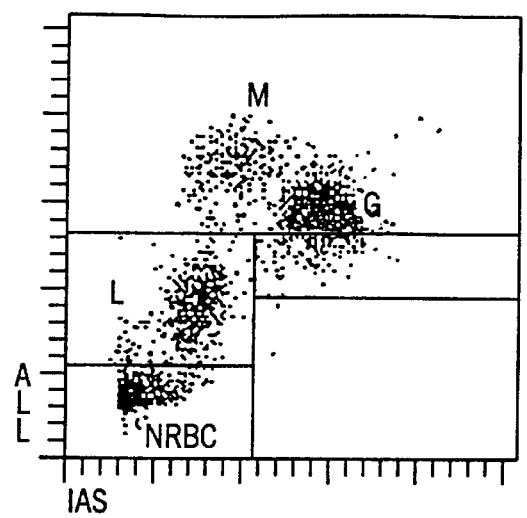
FIGS. 9a–9c are multi-angle, light scatter based analyzer WBC cytograms of normal whole blood spiked with the fixed trout erythrocyte nuclei of FIGS. 8a–8c.
Figure 9B:
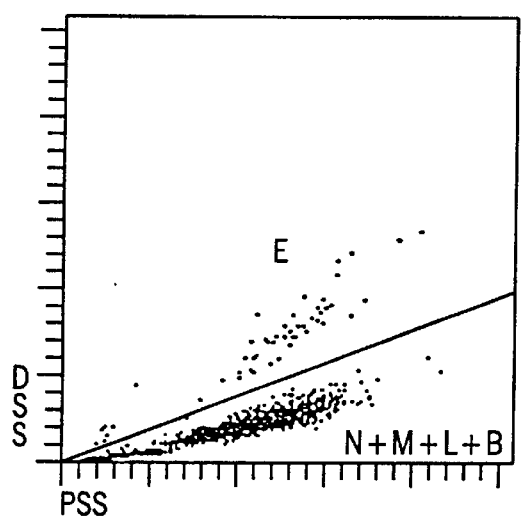
Figure 9C:
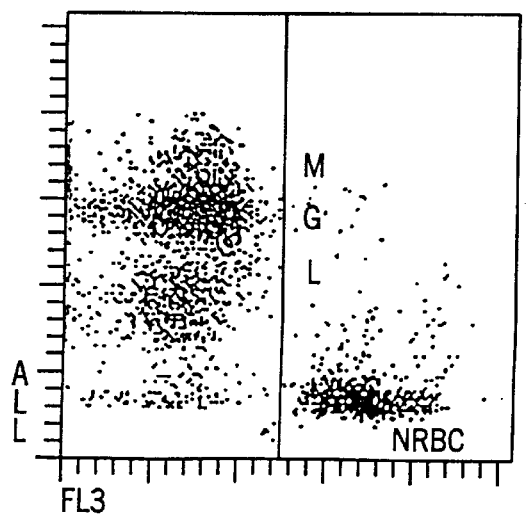
Figure 10A:
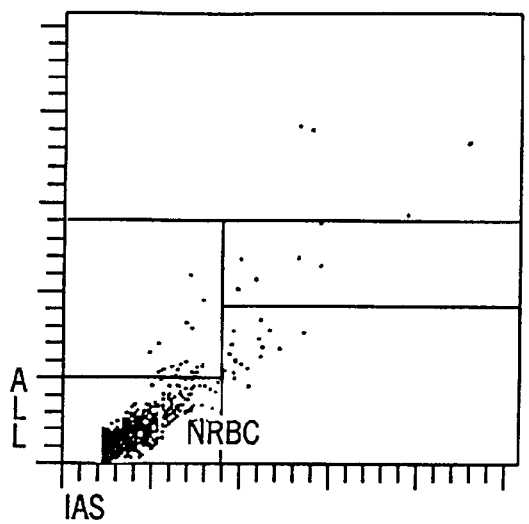
FIGS. 10a–10c are multi angle, light scatter based analyzer WBC cytograms of fixed chicken erythrocyte nuclei produced by the methods of the present invention.
Figure 10B:
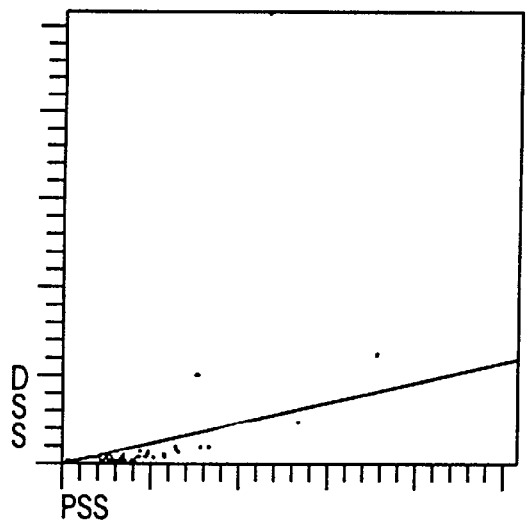
Figure 10C:
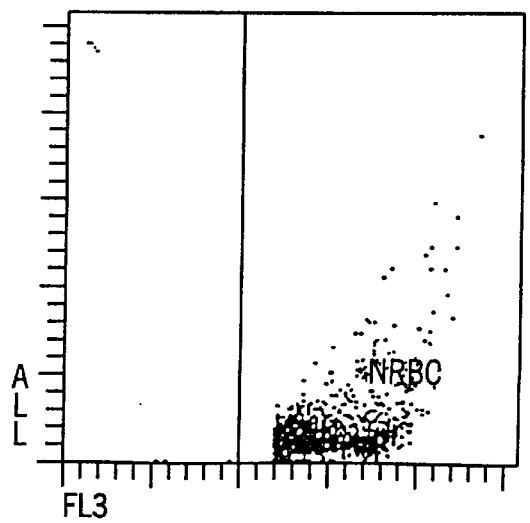
Figure 11A:
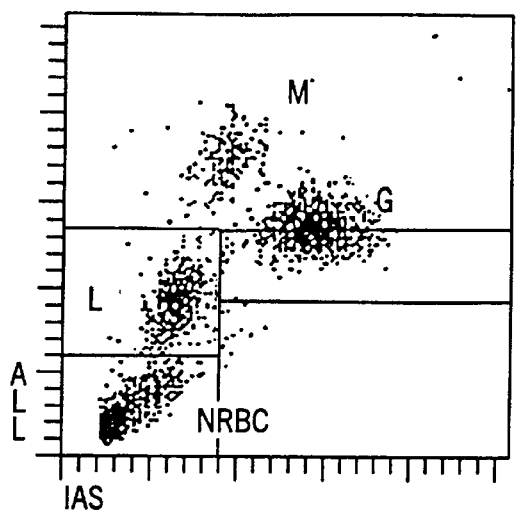
FIGS. 11a–11c are multi-angle, light scatter based analyzer WBC cytograms of whole blood spiked with the fixed chicken erythrocyte nuclei of FIGS. 10a–10c.
Figure 11B:
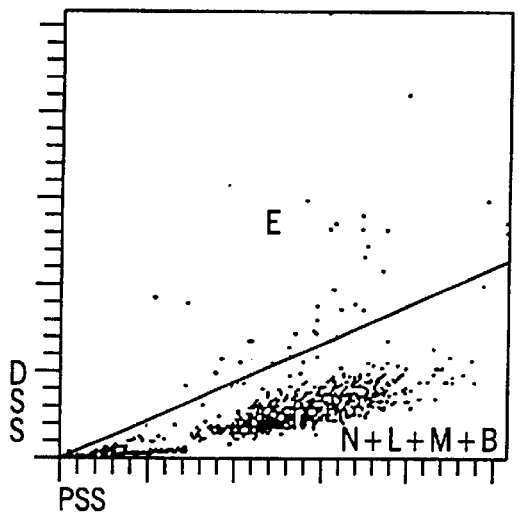
Figure 11C:
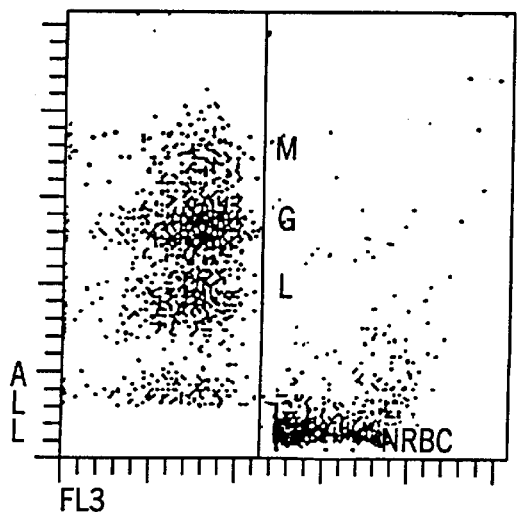
Figure 12A:
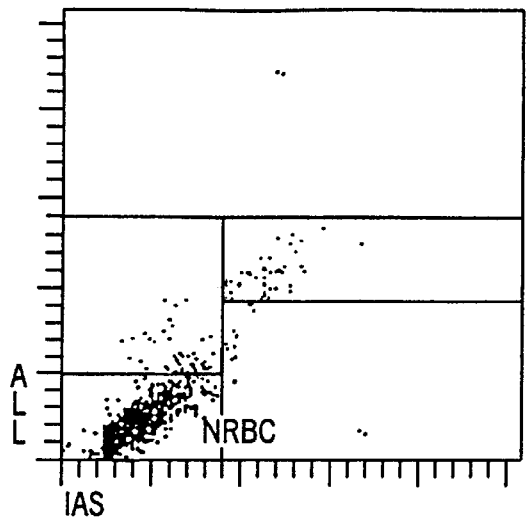
FIGS. 12a–12c are multi-angle, light scatter based analyzer WBC cytograms of fixed turkey erythrocyte nuclei produced by the methods of the present invention.
Figure 12B:
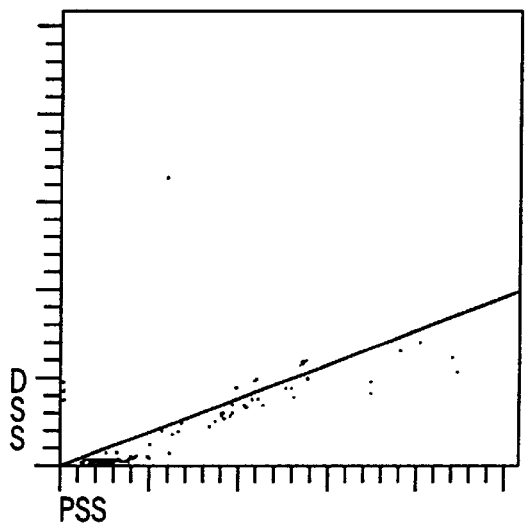
Figure 12C:
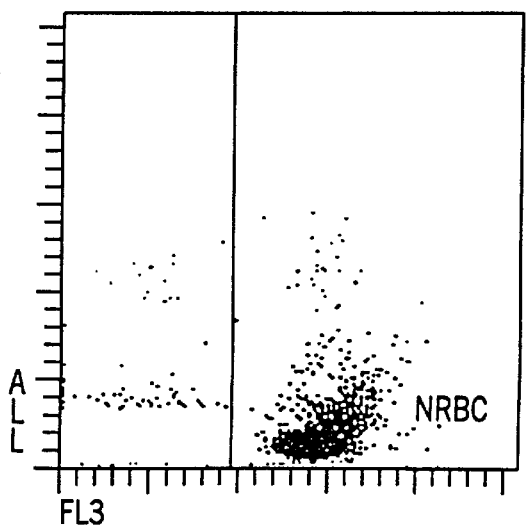
Figure 13A:
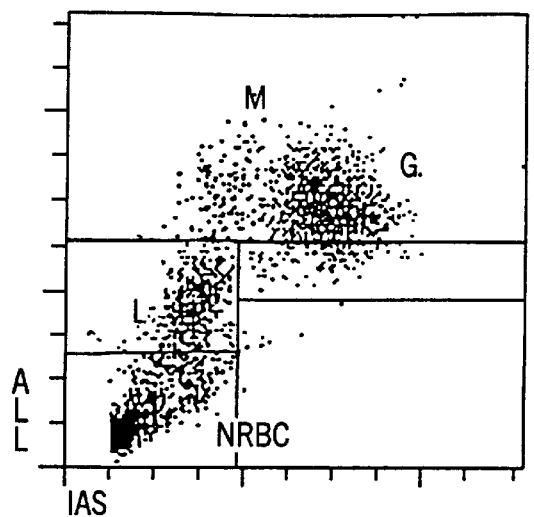
FIGS. 13a–13c are multi-angle, light scatter based analyzer WBC cytograms of whole blood spiked with the fixed turkey erythrocyte nuclei of FIGS. 12a–12c.
Figure 13B:
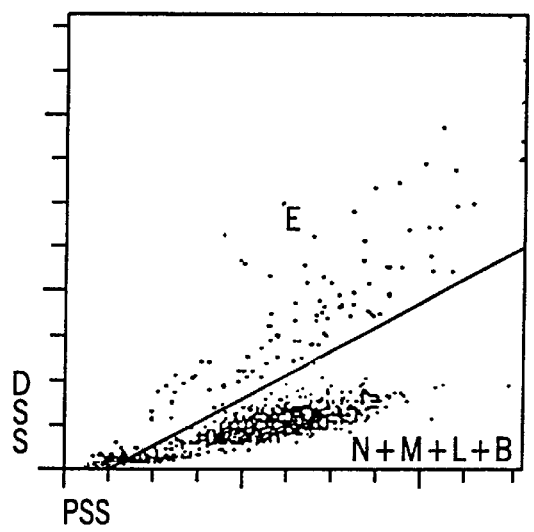
Figure 13C:
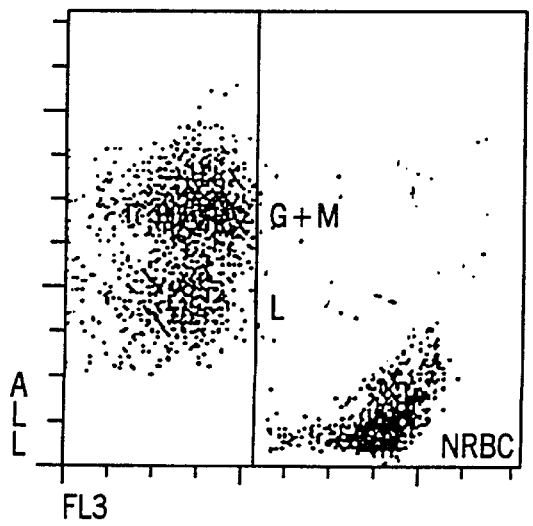

The lysing reagent and fixative described above are used in this example. Stable and clump-free fixed human WBC's were prepared according to the following protocol and an example of the Cell-Dyn® 4000 instrument WBC cytograms of the fixed human WBC of this example are presented as FIGS. 7a–7c.

1. One (1) part of human buffy coat layer was mixed with 5 parts of lysing reagent (pre-warmed at 42° C.). The components were mixed immediately by gentle vortexing and allowed to stand at room temperature for 50 seconds to lyse RBC completely.
2. One part of the lysed WBC suspension in Step 1 was mixed with ten (10) parts of fixative and immediately placed in a 60° to 70° C. water bath and fixed for 10 minutes with gentle mixing.
3. The fixed cell suspension was cooled at room temperature, centrifuged at 2,500 rpm at 10° C. for 5 minutes to remove the Fixative, washed 3 times using the same centrifuge speed with isotonic phosphate buffered saline at neutral pH (PBS) and then resuspended in CRSM.
4. An aliquot of the finished product was run on a Cell-Dyn® 4000 instrument for WBC counts and distribution.
5. The fixed cell concentration was adjusted to a final concentration in the resuspension medium of about 7,500/µL for a normal level control.

EXAMPLE 2

The same lysing and fixing reagents used in Example 1 were used but the RBC lysis and WBC fixation were performed according to the following protocol:

1. One (1) part of human buffy coat layer was mixed immediately by gentle vortexing with 5 parts of lysing reagent solution and allowed to stand at room temperature for 10 minutes to lyse RBC completely.
2. One (1) part of the lysed WBC suspension in Step 1 was mixed with ten (10) parts of Fixative, mixed and allowed to fix at room temperature for 2–3 hrs.
3. The fixed cell suspension was centrifuged at 2,500 rpm at 10° C. for 5 minutes to remove the Fixative, washed 3 times using the same centrifuge speed with phosphate buffered saline at neutral pH, and then resuspended in CRSM.
4. An aliquot of the finished product was run on a Cell-Dyn® 4000 instrument for WBC counts and distribution.
5. The fixed cell concentration was adjusted to final concentration of about 2,000/µL for low level control.

EXAMPLE 3

NRBC fraction was prepared from Turkey erythrocytes according to the following protocol and examples of Cell-Dyn® 4000 instrument NRBC cytograms of the fixed turkey erythrocyte nuclei and a normal human whole blood spiked with the fixed Turkey erythrocyte nuclei are presented in FIGS. 12a–12e and 13a–13c respectively.

A) Materials:
1. Turkey Whole Blood
2. Lysing reagent: The same as in Example 1.
3. Fixative: w/Dextrose: Monosodium phosphate: 4 gram/L, Disodium phosphate: 6.5 grams/L, Formalin: 150 ml/L, Dextrose 100 g/L, pH about 6.8
4. Cell Washing solution: Phosphate Buffered Solution (PBS)
5. CRSM: The same CRSM as listed above B) Protocol for Turkey Erythrocyte Nuclei Fixation:
1. Warm up 10 ml aliquot of the lysing reagent at 37° C.
2. Centrifuge turkey whole blood at 3000 rpm for 10 minutes to separate the plasma layer and remove the buffy coat layer. Add the plasma back to the packed RBC layer and mix.
3. Add 1.0 ml of the RBC layer to the pre-warmed lysing reagent solution, cap and immediately invert mix 3 times. Vortex at full speed for about 10 seconds to help the lysis the cytoplasm of RBC. Let stand at room temperature for about 10 minutes or until the lysis or cytoplasm is complete. Check under the microscope for completeness of the cytoplasm lysis.
4. Centrifuge at 2000 rpm for 15 minutes and siphon off all the supernatant leaving just enough to resuspend the cell button. Resuspend the cells by gentle agitation until no cell clumps are observed.
5. Wash the cells 3 times with PBS using the same centrifugation conditions as in Step 4.
6. Add 10 ml of fixative, mix and immediately place it in the water bath at 60° C. and fix for at least 5 minutes with constant agitation to prevent cell clumping.
7. Leave the cell suspension at room temperature for 30 minutes or overnight.
8. Mix and repeat step 4 & 5 twice.
9. Resuspend the fixed nuclei in CRSM.
10. Run on a Cell-Dyn® 4000 instrument to determine the concentration of FL3+ nuclei and the position of the cluster.

EXAMPLE 4

NRBC fraction was prepared from trout erythrocytes using the same reagents and protocol described in Example 3. Examples of Cell-Dyn® 4000 instrument NRBC cytograms of the fixed trout erythrocyte nuclei and a normal whole blood spiked with the fixed trout nuclei are presented in FIGS. 8a–8c and 9a–9c.

EXAMPLE 5

Figure 14A:
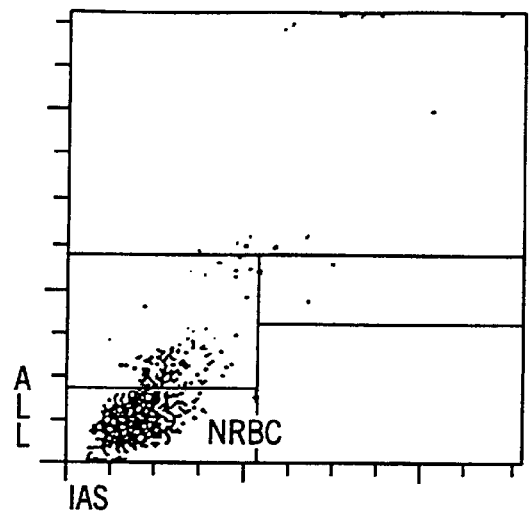
FIGS. 14a–14c are multi-angle, light scatter based analyzer WBC cytograms of fixed porcine lymphocyte nuclei produced by the methods of the present invention.
Figure 14B:
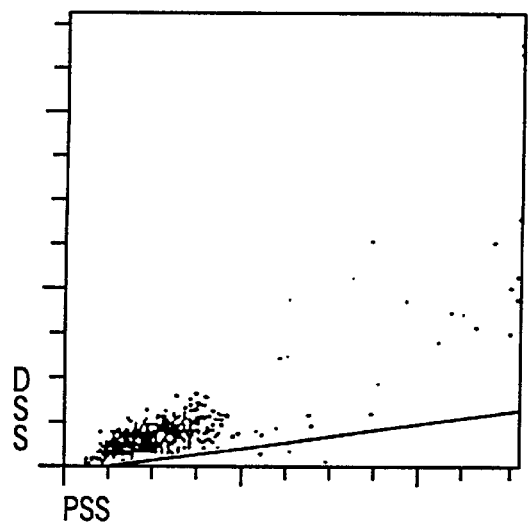
Figure 14C:
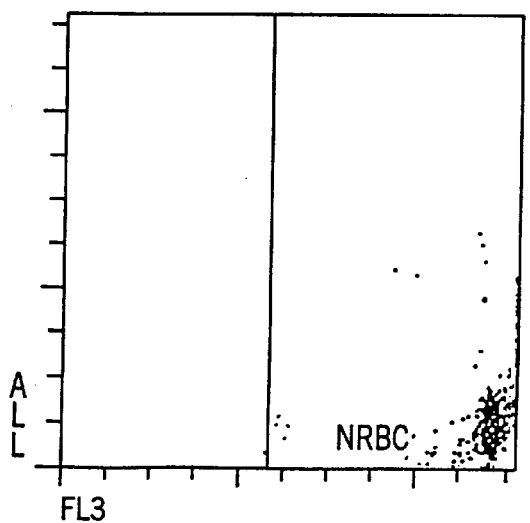
Figure 15A:
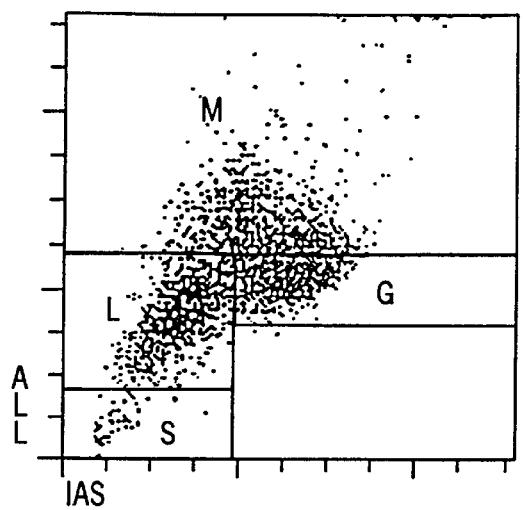
FIGS. 15a–15c are multi-angle, light scatter based analyzer WBC cytograms of fixed bovine WBC by the method of the present invention.
Figure 15B:
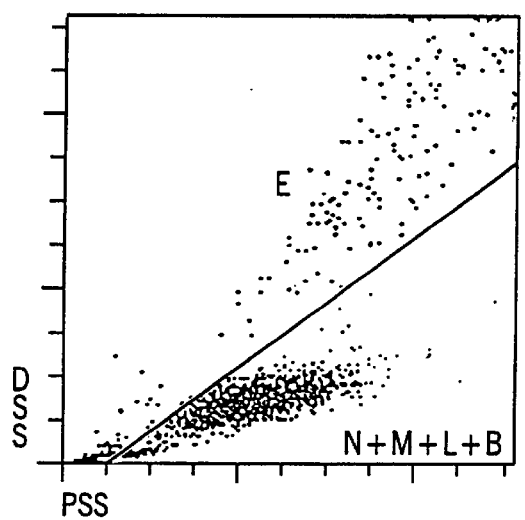
Figure 15C:
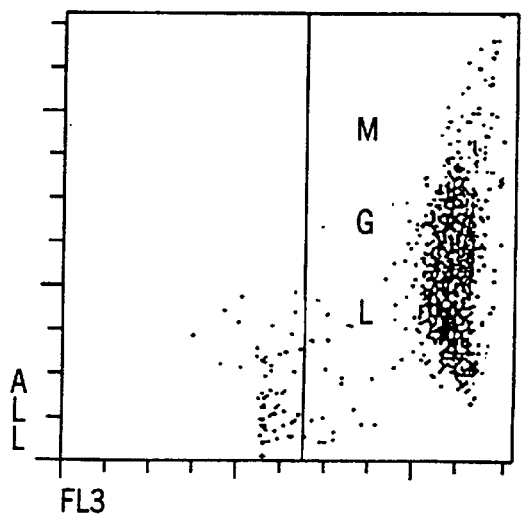
Figure 16A:
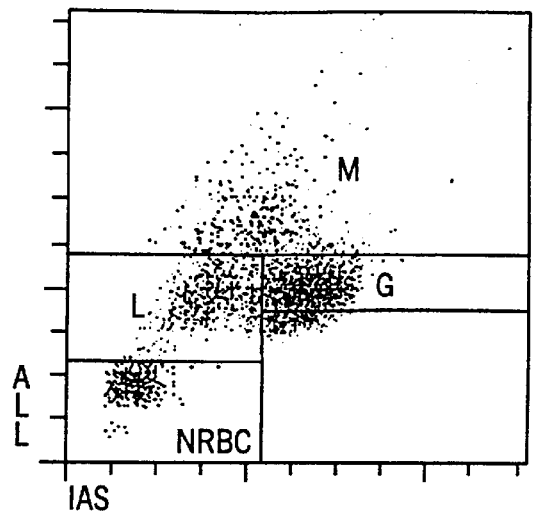
FIGS. 16a–16f are multi-angle, light scatter based analyzer WBC cytograms of fixed bovine WBC spiked with fixed porcine lymphocytes, all produced according to the methods of the present invention.
Figure 16B:
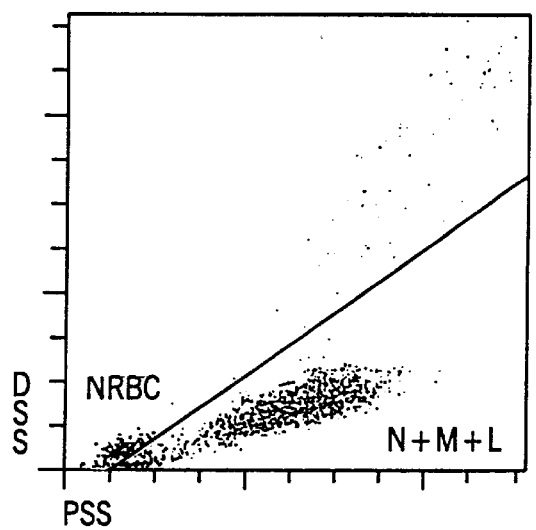
Figure 16C:
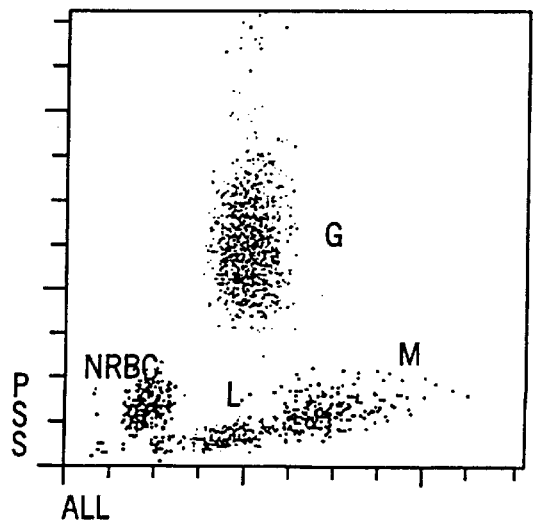
Figure 16D:
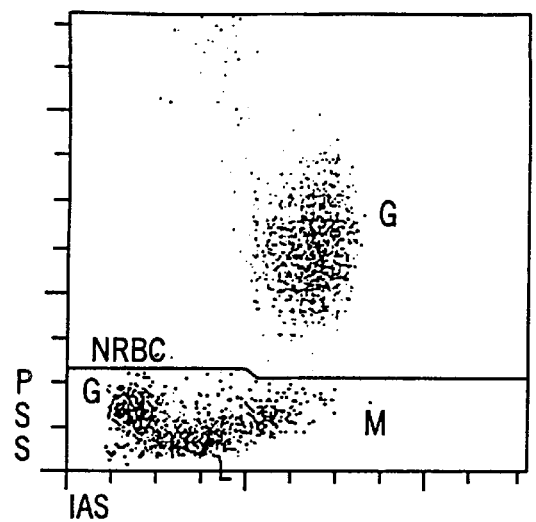
Figure 16E:
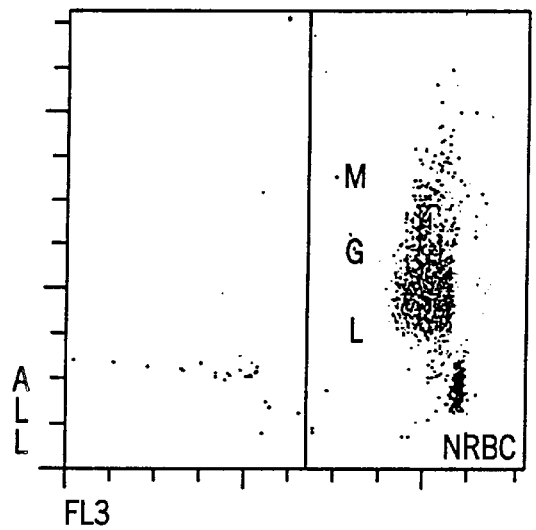
Figure 16F:
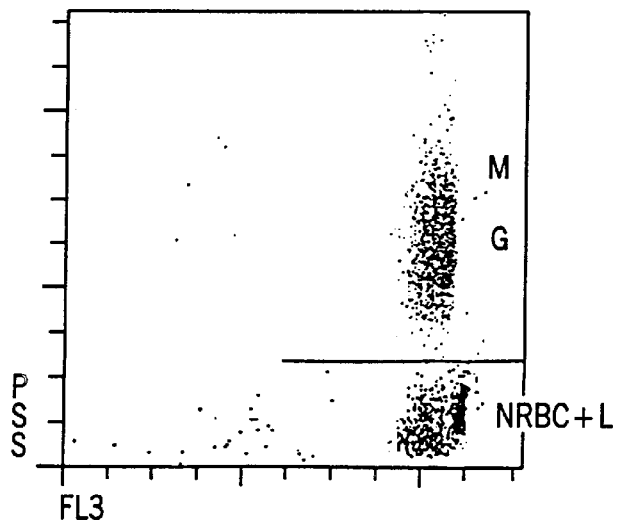
Figure 17A:
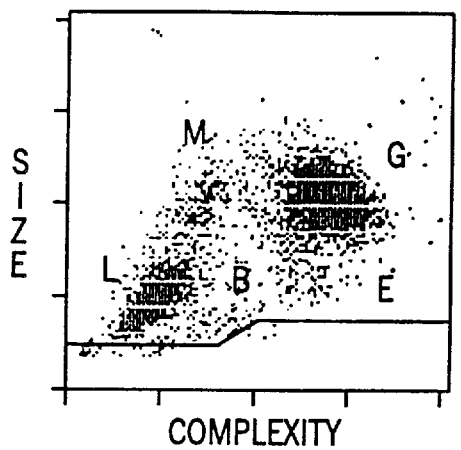
FIGS. 17a–17d are WBC cytograms of fixed bovine WBC produced by the methods of the present invention and run on an analyzer utilizing both impedance and light scatter.
Figure 17B:
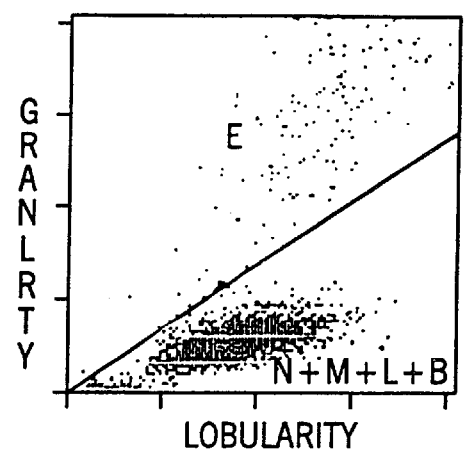
Figure 17C:
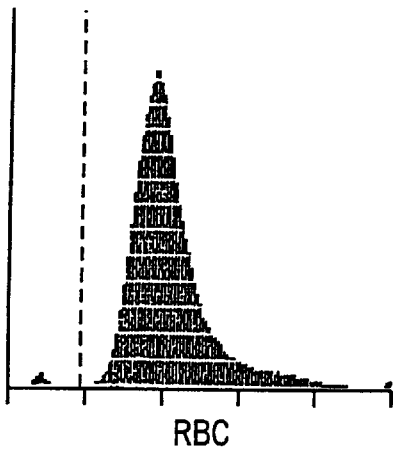
Figure 17D:
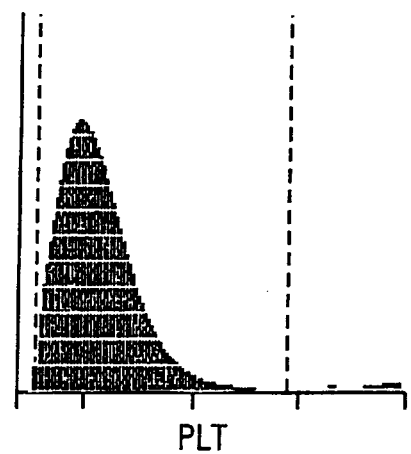
Figure 18A:
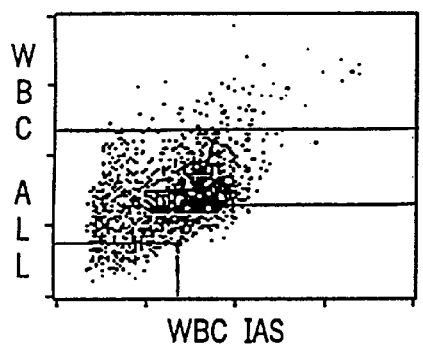
FIGS. 18a–18d are WBC cytograms of a control cell solution containing fixed alligator RBC as the control cells and run on a multi-parameter, light scatter based analyzer.
Figure 18B:
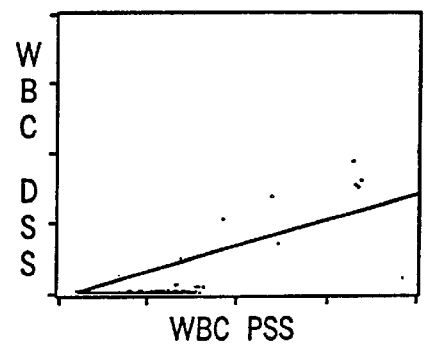
Figure 18C:
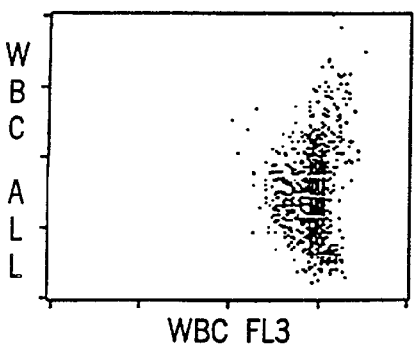
Figure 18D:
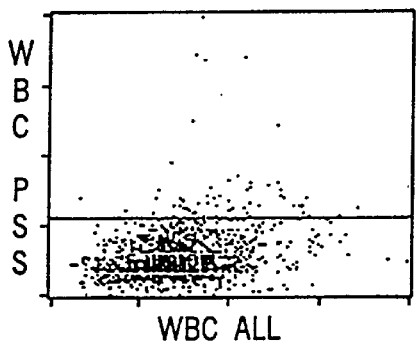

NRBC Fraction was prepared from Porcine Lymphocytes according to the following materials and methods and an example of Cell-Dyn® 4000 instrument NRBC cytograms of the fixed porcine lymphocyte nuclei is presented in FIGS. 14a–14c.
A) Materials:
Porcine buffy coat (platelets already removed) layer.
Cyto-Lyse:
Brij 35: 15.0 g/L
Phthalic Acid 5.5 g/L
Lysing Reagent: the same as in Example 1
Fixative: the same as in Example 1
Phosphate Buffered Saline (PBS)
B) Procedure:
1. Dilute one (1) part of the enriched porcine lymphocyte layer with 5 parts of the lysing reagent and let stand at room temperature for 5 minutes to complete the lysis of the remaining RBC in the cell suspension.
2. Centrifuge the cell suspension 3 minutes at 3000 rpm and pour off the supernatant and dislodge the cell button.
3. Mix the cells with Cyto-Lyse at 1:10 ratio and leave at room temperature for 2 hrs.
4. Resuspend the nuclei in Cyto-Lyse and spin for 3 minutes at 3000 rpm and pour off the supernatant.
5. Resuspend the nuclei in minimum 2 volumes of Fixative and mix.
6. Fix at 60° C. for 10 minutes (or for 4 hrs. at room temperature) and allow to cool at room temperature.
7. Centrifuge the nuclei for 3 minutes at 3000 rpm and pour off supernatant.
8. Re-suspend the cell pellet in PBS to wash the nuclei 3 times.
9. Resuspend the nuclei in CRSM.

EXAMPLE 5

Bovine WBC's are fixed according to the protocol described in Example 1 and mixed with fixed porcine nuclei prepared according to the procedure described in Example 4. Examples of Cell-Dyn® 4000 instrument WBC channel cytograms of the fixed bovine WBC's alone and the fixed bovine WBC's mixed with porcine lymphocyte nuclei are presented in FIGS. 15a–15c and 16a–16f.

EXAMPLE 6

NRBC fraction was prepared from Chicken erythrocytes according to the protocol described in Example 3 and examples of Cell-Dyn® 4000 instrument NRBC cytograms of the fixed Chicken erythrocyte nuclei and a normal human whole blood spiked with the fixed Chicken erythrocyte nuclei are presented in FIGS. 10a–10c and FIGS. 11a–11c.

The hematology control produced by the method of present invention can also be used to monitor the following parameters on Cell-Dyn® 3000 or 3500 instruments, which utilize both light scatter and impedance signals, to monitor the following WBC/Diff parameters:

| Parameter | Absolute Cell Counts | % of Total WBC |
| --- | --- | --- |
| Total WBC | # of cells/mL | % of Total WBC |
| Neutrophils | # of cells/mL | % of Total WBC |
| Lymphocytes | # of cells/mL | % of Total WBC |
| Eosinophils | # of cells/mL | % of Total WBC |
| Monocytes | # of cells/mL | % of Total WBC |
| Basophils | # of cells/mL | % of Total WBC |

FIGS. 17a–17d are WBC cytograms of fixed bovine WBC produced by the methods of the present invention and run on a Cell-Dyn® 3500 analyzer that conducts the WBC/Diff analysis using light scatter parameters (but no axial light loss or fluorescence) and determines RBC and platelets by means of impedance. For this figure the WBC fraction was combined with fixed platelets and stabilized, but unfixed RBC to produce a full range control suspension.

We claim:
1. A method of producing a white blood cell ("WBC") fraction of a hematology control solution such that the WBC fraction retains its light scatter capabilities, the method comprising:
  a. providing mammalian whole blood or buffy coat layer;
  b. combining the whole blood or buffy coat layer with a lysing reagent for from about 1 to 5 minutes in a ratio of from about 1 part blood or buffy coat layer to about

12 parts lysing reagent to eliminate any red blood cells present and to form a cell suspension, wherein the lysing reagent is present in an amount from about 1 part lyse to about 12 parts diluent;

c. combining the cell suspension of step b with a fixative to form a mixture and incubating the mixture at from about 60° C. to about 70° C. for up to about 10 minutes to fix and stabilize the cells;

d. cooling the mixture of step c to ambient temperature and allowing to sediment;

e. discarding a supernatant formed in step d and washing the resultant fixed cells sufficient to remove the active reagents of steps b and c; and f. resuspending the fixed and washed cells in a resuspension medium suitable for long term storage of the fixed cells, wherein the fixed cells exhibit multi-angle light scattering characteristics similar to the multi-angle light scattering characteristics of WBC of interest so that subpopulations of WBC may be differentiated with the control solution solely by the use of a multi-angle light scatter hematology analyzer.

2. A method of producing a nucleated red blood cell fraction of a hematology control solution for use on a multi-angle light scatter hematology analyzer comprising:

a. providing whole blood or a red blood cell layer selected from the group consisting of avian and fish erythrocytes;

b. combining the erythrocytes or whole blood with a lysing reagent for from about 1 to 5 minutes in a ratio of from about 1 part erythrocyte or blood to about 12 parts lysing reagent to form a cell suspension;

c. combining the cell suspension of step b with a fixative to form a mixture and incubating the mixture at from about 60° C. to about 70° C. for up to about 10 minutes to fix and stabilize nuclei from the cells, wherein the ratio of fixative to cell suspension is from about 1:8 to about 1:11;

d. cooling the mixture of step c to ambient temperature and allowing the suspension to sediment;

e. discarding a supernatant formed in step d. and washing the resultant fixed nuclei sufficient to remove the active reagents of steps b and c; and f. resuspending the fixed and washed nuclei in a resuspension medium suitable for long term storage of the fixed nuclei.

3. A method of producing a nucleated red blood cell fraction of a hematology control solution for use on a multi-angle light scatter hematology analyzer comprising:

a. providing mammalian lymphocytes;

b. mixing the lymphocytes and a lysing reagent for from about 5 minutes to about 3 hours in a ratio of from about 1:5 lymphocytes to lysing reagent to from about 1:30 lymphocytes to lysing reagent to expose the nuclei of the lymphocytes and form a nuclei suspension;

c. combining the nuclei suspension of step b with a fixative to form a mixture and incubating the mixture at from about 55° C. to about 60° C. for up to about 10 minutes to fix and stabilize the nuclei, wherein the ratio of fixative to nuclei suspension is from about 1:1 to about 1:10;

d. cooling the mixture of step c to ambient temperature and allowing the suspension to sediment;

e. discarding a supernatant formed in step d and washing the resultant fixed nuclei sufficient to remove the active reagents of steps b and c; and f. resuspending the fixed and washed nuclei in a resuspension medium suitable for long term storage of the fixed cells.

* * * * *